United States Patent
Bae et al.

(10) Patent No.: US 7,403,019 B2
(45) Date of Patent: Jul. 22, 2008

(54) APPARATUS AND METHOD OF WATER ABSORPTION TEST FOR GENERATOR STATOR WINDING INSULATOR USING CROSS CAPACITANCE

(75) Inventors: Yong-Chae Bae, Daejeon Metropolitan (KR); Hee-Soo Kim, Daejeon Metropolitan (KR); Hyun Lee, Daejeon Metropolitan (KR); Yeon-Whan Kim, Daejeon Metropolitan (KR); Doo-Young Lee, Daejeon Metropolitan (KR)

(73) Assignee: Korea Electric Power Corporation, Seoul (KR)

( * ) Notice: Subject to any disclaimer, the term of this patent is extended or adjusted under 35 U.S.C. 154(b) by 0 days.

(21) Appl. No.: 11/464,675

(22) Filed: Aug. 15, 2006

(65) Prior Publication Data
US 2008/0001610 A1    Jan. 3, 2008

(30) Foreign Application Priority Data
Jun. 30, 2006    (KR)    ........................ 10-2006-0060385

(51) Int. Cl.
*G01R 27/00*    (2006.01)

(52) U.S. Cl. ............... 324/664; 324/694; 324/76.11
(58) Field of Classification Search ............ 324/664, 324/644, 694, 76.11
See application file for complete search history.

(56) References Cited

U.S. PATENT DOCUMENTS

| | | | |
|---|---|---|---|
| 3,826,979 A * | 7/1974 | Steinmann | 361/178 |
| 6,020,744 A * | 2/2000 | Ghorashi et al. | 324/678 |
| 6,407,474 B1 | 6/2002 | Mahn et al. | |
| 6,530,066 B1 | 3/2003 | Ito et al. | |
| 2003/0222662 A1 * | 12/2003 | Geisel | 324/664 |

* cited by examiner

*Primary Examiner*—Vincent Q. Nguyen
(74) *Attorney, Agent, or Firm*—Morgan & Finnegan LLP

(57) ABSTRACT

Apparatus and method of water absorption for generator stator winding insulator using a cross capacitance are disclosed. The apparatus includes a sensor using a cross capacitance, and a water absorption testing unit for carrying out the water absorption test of the insulator of the stator winding of the power generator using the sensor. The apparatus determines whether the insulator absorbs water, according to thickness, using the cross capacitance, such that inferior winding is detected, a power plant is prevented from being suddenly stopped, costs for the maintenance are reduced, and the lifespan of the power generator is extended.

4 Claims, 9 Drawing Sheets

| Dummy Sample | Mode | Fef(A/H) | Circuit(KEPCO) | $\frac{(C_1 - C_2)}{C_1} \times 100\,(\%)$ |
|---|---|---|---|---|
| Teflon<br>t = 4.13 | S | 10.44 | 10.43 | −0.09 |
|  | D | 7.11 | 7.12 | 0.14 |
|  | Q | 4.21 | 4.22 | 0.23 |
| Epoxy<br>t = 3.2 | S | 14.72 | 14.75 | 0.20 |
|  | D | 9.72 | 9.71 | −0.1 |
|  | Q | 5.47 | 5.46 | −0.18 |
| Mica<br>t = 4.0 | S | 17.25 | 17.35 | 0.56 |
|  | D | 11.22 | 11.28 | 0.53 |
|  | Q | 6.20 | 6.22 | 0.32 |
| Al$_2$O$_3$<br>t = 3.0 | S | 21.3 | 21.27 | −0.14 |
|  | C | 13.9 | 13.88 | −0.14 |
|  | Q | 7.45 | 7.42 | −0.4 |

FIG.17

| Dummy Sample | Mode | Fef(A/H) | Circuit(KEPCO) | $\frac{(C_1 - C_2)}{C_1} \times 100\,(\%)$ |
|---|---|---|---|---|
| Teflon t = 4.13 | S | 15.27 | 15.14 | 0.85 |
| | D | 9.54 | 9.66 | 1.25 |
| | Q | 5.33 | 5.41 | 1.5 |
| Epoxy t = 3.2 | S | 21.13 | 21.14 | 0.04 |
| | D | 13.10 | 13.24 | 1.07 |
| | Q | 7.06 | 7.12 | 0.85 |
| $Al_2O_3$ t = 3.0 | S | 30.71 | 30.67 | 0.13 |
| | C | 19.78 | 20.17 | 1.97 |
| | Q | 10.63 | 10.8 | 1.59 |

APPARATUS AND METHOD OF WATER ABSORPTION TEST FOR GENERATOR STATOR WINDING INSULATOR USING CROSS CAPACITANCE

BACKGROUND OF THE INVENTION

1. Field of the Invention

The present invention relates to water absorption test for an insulator of a stator winding of a power generator, and more particularly, to a water absorption testing apparatus of an insulator of a stator winding of a power generator using a cross capacitance in which a deteriorated winding is detected by determining whether or not the insulator of the stator winding of a power generator absorbs cooling water according to thickness using the cross capacitance such that a power station is prevented from being suddenly stopped, costs for the maintenance are reduced, and the lifespan of the power generator is extended.

2. Description of the Related Art

Generally, a high capacity power generator is a water cooling type generator, and heat generated while making electricity is cooled by water. Particularly, for the cooling of a stator winding of the generator, pure water having a high efficiency is used.

However, when an insulator of the stator winding of the generator absorbs moisture or water, insulation is broken during the operation of the generator thereby causing accident of the unwanted generator trip. Thus, the operation reliability of the generator is deteriorated, costs and time for replacing the winding with new one are increased so that the productivity of generating electricity is deteriorated.

As a conventional method of water absorption test for generator stator winding insulator, there is a tan δ test and a method of measuring general capacitance between two plates for the diagnosis.

Here, the tan δ is a dielectric tangent, while the dielectric tangent (tan δ) is a tan function of a phase difference (δ) of a dielectric substance between perfect capacitive current and measured current. Since an ideal dielectric substance has only capacitance components, δ may be 90 degrees. Thus, the tan δ may be infinite value. However, when the dielectric substance is inferior, resistance component is generated so that δ is less than 90 degrees. The dielectric tangent test uses the point that a loss is generated when an AC voltage is applied to the insulator. This loss is divided into a loss due to a leak current, a loss due to dielectric polarization, and a loss due to partial discharge. Because of these losses, overall current is delayed more than a charged current component, while this delayed angle is known as a dielectric loss angle, and the tangent thereof is known as the dielectric tangent. When an applied voltage is known, the capacitance can be known, and when the loss angle is known, the loss can be known.

However, the tan δ can determine whether or not the insulation of the phase of the winding is good, but cannot determine whether or not the water absorption has occurred in respective windings.

Moreover, in the method of measuring the general capacitance between two plates for the diagnosis, the water absorption of the insulator of the winding can be determined. However, an error with respect to variation of thickness of the winding insulator is likely to be generated in the testing apparatus during the water diagnosis. Additionally, since stray capacitance generated during the measurement cannot be removed, there is no solution of avoiding the error.

Moreover, there is no measuring information of the tan δ with respect to the respective windings, and the water absorption of the insulator of the stator winding of the generator cannot be measured in relation to the thickness.

Therefore, in order to solve the above technical problem, in the present invention, a water absorption testing apparatus is developed by applying a cross capacitance theory to the water absorption test of the insulator of the stator winding of a generator.

SUMMARY OF THE INVENTION

Therefore, the present invention has been made in view of the above and/or other problems, and it is an object of the present invention to provide water absorption testing apparatus of an insulator of a stator winding of a power generator, using a cross capacitance, in which a deteriorated winding is detected by determining whether or not the insulator of the stator winding of a power generator absorbs cooling water according to thickness, using the cross capacitance, such that a power plant is prevented from being suddenly stopped, costs for the maintenance are reduced, and the lifespan of the power generator is extended.

In accordance with the present invention, the above and other aspects can be accomplished by the provision of an apparatus of water absorption for generator stator winding insulator using a cross capacitance, including a sensor measuring a cross capacitance, and a water absorption testing unit for carrying out the water absorption test of the insulator of the stator winding of the power generator using the sensor.

In accordance with the present invention, the above and other aspects can be accomplished by the provision of a method of water absorption for generator stator winding insulator using a theory of the cross capacitance, and carrying out the water absorption test of the insulator of the stator winding of the power generator using the detected state in the detecting.

BRIEF DESCRIPTION OF THE DRAWINGS

These and/or other aspects and advantages of the present invention will become apparent and more readily appreciated from the following description of the embodiments, taken in conjunction with the accompanying drawings, in which:

FIG. 17 is a table listing measured results in a case of designing a circuit for driving the sensor in FIG. 12 by taking the sensor into consideration.

DESCRIPTION OF THE PREFERRED EMBODIMENTS

Hereinafter, a water absorption testing apparatus of an insulator of a stator winding of a power generator using a cross capacitance and a method of testing water absorption according to the embodiments of the present invention will be described in detail with reference to the accompanying drawings.

Figure 2:
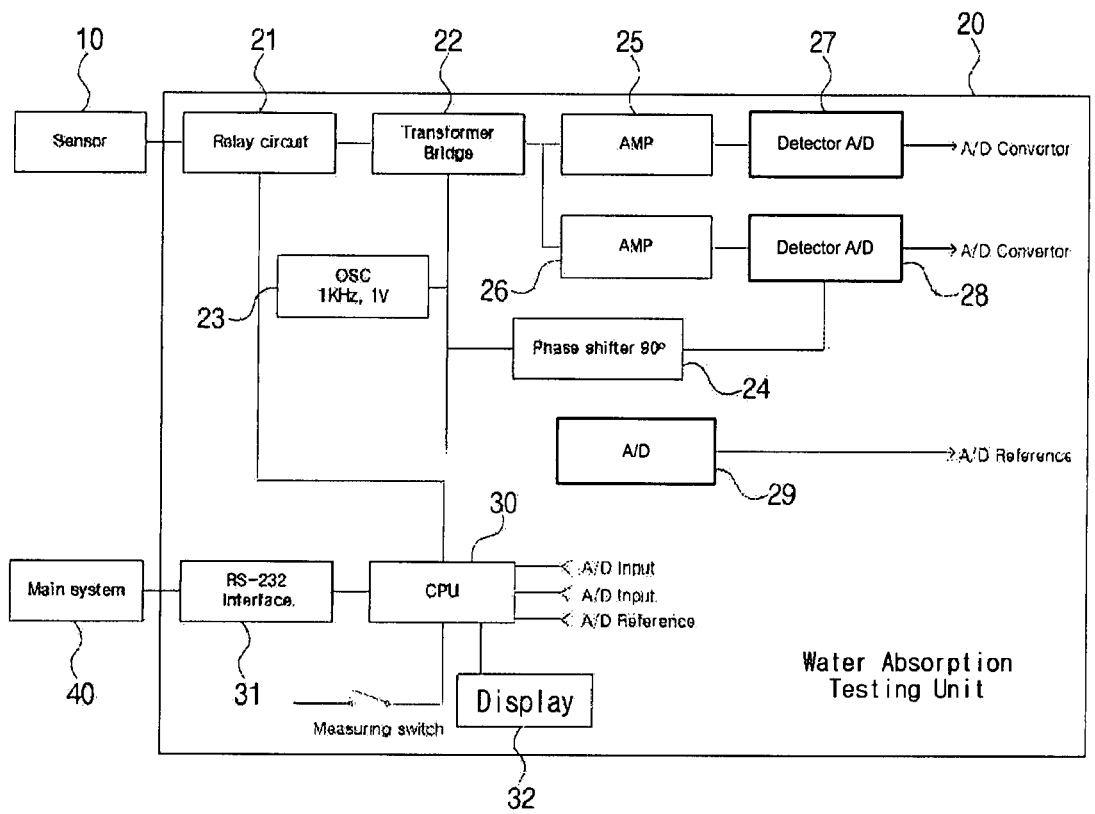
FIG. 2 is a block diagram illustrating an apparatus for testing water absorption of an insulator of a stator winding of a power generator using cross capacitance according to a first embodiment of the present invention.

Firstly, the water absorption testing apparatus of an insulator of a stator winding of a power generator using a cross capacitance according to an embodiment of the present invention, as shown in FIG. 2, includes a sensor 10 using the cross capacitance, and a water absorption testing unit 20 for carrying out the water absorption test for the insulator of the stator winding using a value measured by the sensor 10.

The sensor 10, in order to measure a capacitance and a dielectric tangent of an insulator of a stator winding of a generator according to thickness, includes at least one of a single electrode, a double electrode, and a quadruple electrode, and the electrodes are planar types in which a high, a ground, and a low, and a ground are sequentially arranged.

The sensor 10 is characterized in that guard electrodes are inserted between the respective electrodes.

The sensor 10, as shown in FIG. 9, is configured by the single electrode, the double electrode, and the quadruple electrode to measure the capacitance and the dielectric tangent of the insulator of the stator winding of the generator according to the thickness. In this case, the electrodes are arranged in the form of the planar type. When measuring the capacitance and the dielectric tangent according to the thickness, firstly the sensor 10 becomes the single electrode to measure the capacitance corresponding to a thickness d2 due to the single electrode, next the sensor 10 becomes the double electrode to measure the capacitance corresponding to the thickness d2 due to the double electrode, and finally the sensor 10 becomes the quadruple electrode to measure the capacitance of the quadruple electrode corresponding to a thickness d3 with respect to the quadruple electrode.

The sensor 10 sets the cross capacitor as the following formula, $$\exp(-\pi C_{ac}/L\varepsilon_0) + \exp(-\pi C_{bd}/L\varepsilon_0) = 1$$

$$C = \frac{\varepsilon_0 \cdot \ln 2}{\pi} \times L = 0.001953549 \text{ pF/mm}$$

where, $C_{ac}$ and $C_{bd}$ are electrostatic capacitances between electrodes facing each other, L is a length of a cylinder in the axial direction, and $\varepsilon_0$ is a vacuum permittivity.

The water testing unit 20 includes a relay circuit 21 for relaying a signal between the sensor and a CPU 30, a transformer bridge 22 for receiving a signal from the sensor 10 through the relay circuit 21 and branching the same, an oscillator 23 connected to the transformer bridge 22 to supply a local oscillator frequency, a phase shifter 24 for shifting a phase of the signal from the sensor received from the transformer bridge 22 by 90 degrees with reference to the frequency received from the oscillator 23, first and second amplifiers 25 and 26 for receiving a signal detected by the sensor 10 from the transformer bridge 22 and amplifying the same, a first detector 27 for transforming an analog signal of the sensor amplified by the first amplifier 25 into a digital signal, a second detector 28 for transforming an analog signal of the sensor 10 amplified by the second amplifier 26 into a digital signal required for the 90 degree phase shift by the phase shifter 24, and A/D converter 29 for converting the analog signals of the oscillator 23 into digital signals, the CPU 30 for receiving the signals of the sensor 10 converted into the digital signals by the first and second detectors 27 and 28 and a reference signal from the A/D converter 29 and for carrying out the water absorption test of the insulator of the stator winding of the generator, and an interface 31 for connecting a main system 40 to the water absorption testing unit 20.

The CPU 30 automatically switches and selects the single electrode, the double electrode, and the quadruple electrode of the sensor 10 through the relay circuit 21.

The water absorption testing unit 20 includes a display 32 connected to the CPU 30 to display a result measured by the CPU 30.

The display 32 selects and displays at least one of menus such as (1) Measurement, (2) Data display, (3) Data transmission, and (4) Calibration as a main menu.

The water absorption testing method of an insulator of a stator winding of a power generator using a cross capacitance, according to an embodiment of the present invention, comprising, detecting a state of the insulator of the stator winding of the generator using the theory of the cross capacitance, and carrying out the water absorption test of the insulator of the stator winding of the generator using the detected state, in detection.

In the detecting, in order to measure the capacity and the dielectric tangent of the insulator of the stator winding of the generator according to the thickness, when the sensor 10 includes the single electrode, the double electrode, and the quadruple electrode, while the electrodes are arranged in the planar types and the measurement for the insulator of the stator winding of the generator is carried out according to the thickness, firstly the sensor 10 becomes the single electrode and measures the capacity corresponding a thickness d1 caused by the single electrode, next the sensor 10 becomes the double electrode and measures the capacity corresponding to a thickness d2 caused by the double electrode, and finally the sensor 10 becomes the quadruple electrode and measures the capacity corresponding to a thickness d3 caused by the quadruple electrode, so that the state of the insulator of the stator winding of the generator is detected.

The water absorption testing apparatus and method of the insulator of the stator winding of the generator using the cross capacitance according to the embodiments of the present invention will be described in detail with reference to the drawings as follows. In the following description of the present invention, when the detailed description of the already known structure and operation may confuse the subject matter of the present invention, the detailed description thereof will be omitted. Moreover, terminologies defined by taking functions in the present invention into a consideration, may be changed by a user, the purpose of an operator, or a case law. Thus, the respective terminologies should be interpreted through the whole specification of this application.

Firstly, the present invention is made for the purpose of detecting a deteriorated winding by determining, whether or not the insulator of the stator winding of the power generator absorbs cooling water, according to thickness, using the cross capacitance, to prevent a power plant from being suddenly stopped, to reduce costs for the maintenance, and to extend the lifespan of the power generator.

1. Introduction

Generally, a stator winding of a power generator includes a copper conductor for conduction and a mica coating for insulation around the copper conductor. In order to cool heat generated from the copper conductor, water cooling type cooler is employed such that water passes through inner holes formed in the copper conductor. Due to the reason, such as crevice corrosion generated between brazed portions, delamination of the insulator, the water passing through the inner holes in the copper conductor may permeate into the insulator and cause a serious accident in the generator. As methods of detecting water leakage used nowadays, there are an insulation diagnosis test, a pressure test, and a vacuum test. However, even when the test result is accurately determined, the water absorption of the winding may break the insulation.

Figure 1:
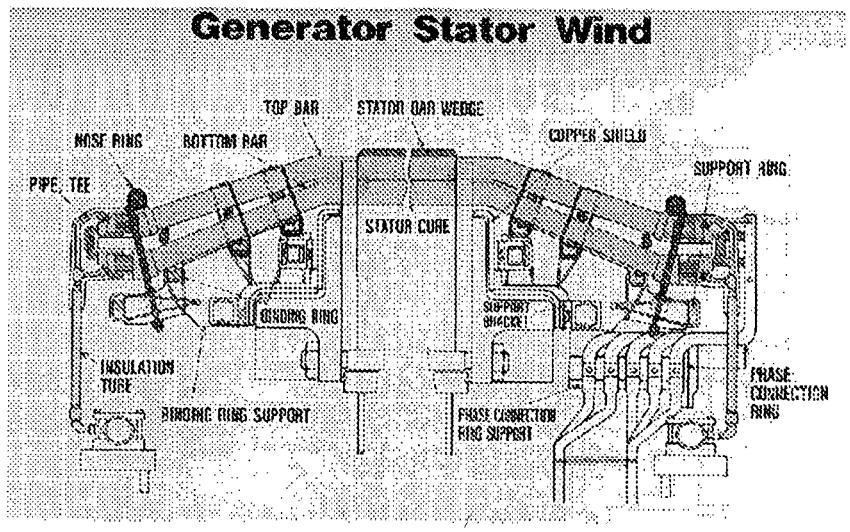
FIG. 1 is a conceptual view illustrating a conventional stator winding of a power generator.

FIG. 1 is a conceptual view illustrating a conventional insulator of a stator of a power generator.

A water absorption tester for measuring capacitance of an insulator between electrodes facing each other and configured by a mica coating of a winding and a copper conductor of the winding has been developed. However, there are several problems when the conventional capacity measuring methods are applied to determine whether the insulator of the stator winding of the generator absorbs moisture.

Here, the capacitance of the insulator between the facing electrodes is $$Cap = \kappa \frac{\varepsilon A}{d},$$

where k is a constant, $\in$ is a dielectric constant, A is the area of a sensor, and d is thickness. Thus, according to the conventional art, when the thickness d of the respective windings to be meassured is not uniform, the capacitance is changed. As such, according to the present invention, since the thicknesses d1, d2, and d3 are determined in accordance with the single electrode, the double electrode, and the quadruple electrode regardless of the thickness between the copper conductor and the sensor 10, there is not an error due to the total thickness change.

In other words, in order to determine the capacitance using the difference of relative dielectric constants varied due to the cooling water contained in the insulator, it must assume that the thickness of the insulator is uniform. However, since the thickness of the insulator of the stator winding is not uniform, the error occurs.

Moreover, an electrode, installed between the sensor and the copper conductor and parallel thereto must be grounded to the copper conductor in order to use the electrode. In this case, since a length of a wire for connecting the copper conductor of the stator winding to a measuring device is very long, according to the theory of measuring the capacitance, the effect of excessive dissipation factor generated from the wire itself cannot be avoided.

Furthermore, the sensor and the measuring device cannot remove stray capacitance generated in the measuring condition.

As such, in order to compensate the error inevitably generated when using the conventional water absorption testing apparatus and the sensor, a capacitance sensor system, that is, Gen-SWAD II (Generator Stator Water Absorption Detector II), to which a cross capacitance measuring principle is applied, has been developed like the present invention.

For the description of the present invention, the cross capacitance principle will be described as follows.

2. Building a Theory.

The principle of the cross capacitor is based on a theorem by Thompson and Lampard, in Australian National measurement Laboratory. As this new electrostatic theory is proposed, a highly precise absolute measurement of an electric capacity is enabled. Nowadays, the cross capacitor is used as a prototype standard in the units of the electric capacity and electric resistance.

Figure 4:
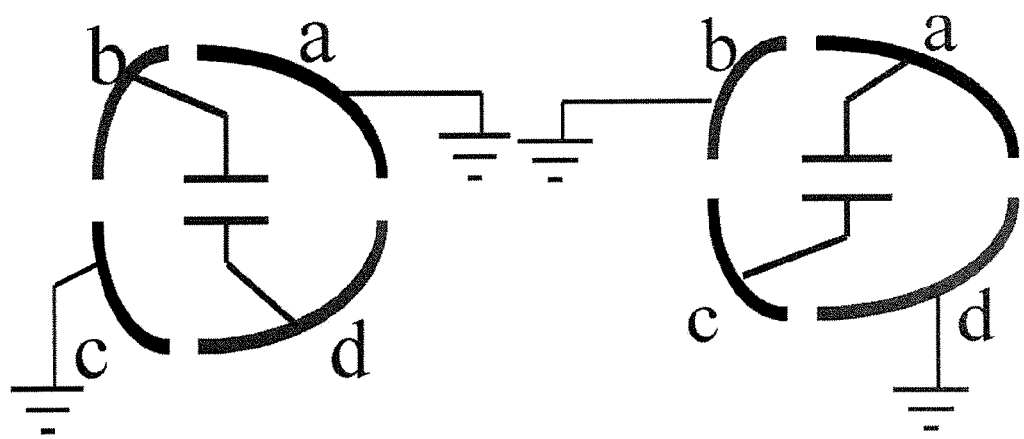
FIG. 4 is a view illustrating a sensing principle, of the sensor, carried out with the cross capacitor in FIG. 2.

FIG. 4 is a view illustrating a sensing principle of the sensor carried out the cross capacitor in FIG. 2.

In a case of dividing a cylinder having a vertical cross-section as shown in FIG. 4 into four narrow insulator gaps, when the relationship between an electric capacity C1 per unit length when electrode of a capacitor C2 is grounded and an electric capacity C2 per unit length when an electrode of a capacitor C1 is grounded is expressed by the esu (Electro Static Unit) of CGS (centimeter-gram-second system), the following formula 1 is established when a space between the electrodes is vacuum regardless of the shape of the cross-section of the cylinder.

$$e^{-4\pi^2 C_2} + e^{-4\pi^2 C_2} = 1 \quad \text{[Formula 1]}$$

The formula 1 is known as a Thompson-Lampard theorem. When this formula is expressed by SI (The International System of Units), the following formula 2 is established.

$$e^{-\frac{\pi}{\varepsilon_0} C_1} + e^{-\frac{\pi}{\varepsilon_0} C_2} = 1 \quad \text{[Formula 2]}$$

In the year 1957, Lampard reported this new electrostatic theory in detail. If $C_1 = C_2 = C_3$, that is, the electrode structure is completely symmetric in the formula 1, the formula 1 becomes the following formula 3.

$$C = \frac{\ln 2}{4\pi^2} \text{esu/cm} = \frac{\varepsilon_0 \ln 2}{\pi} F/m \quad \text{[Formula 3]}$$

However, since generally $C_1 \neq C_2$, $\Delta C = C_1 - C_2$, and if an average value is $C_m = (C_1 + C_2)/2$, the following formula 4 can be expressed.

$$C_1 = C_m + \frac{\Delta C}{2} \quad \text{[Formula 4]}$$
$$C_2 = C_m - \frac{\Delta C}{2}$$

Moreover, when the formula 4 is applied to the formula 2, the following formula 5 is established.

$$\exp\left[-4\pi^2\left(C_m + \frac{\Delta C}{2}\right)\right] + \exp\left[-4\pi^2\left(C_m - \frac{\Delta C}{2}\right)\right] = 1$$

However, since $4\pi_2 = \ln 2 / C$, the formula 5 becomes the following formula 6.

$$C_m = C\left[1 + \frac{\ln 2}{8}\left(\frac{\Delta C}{C}\right)^2 - \frac{(\ln 2)^3}{192}\left(\frac{\Delta C}{C}\right)^2 + \Lambda\right] \quad \text{[Formula 6]}$$

If $\Delta C/C < 3.4 \times 10^{-4}$ in the formula 6, since the second term becomes an error less than $10^{-8}$, it can be disregarded. Thus, the formula 6 can be expressed by the following formula 7.

$$\begin{aligned}C_m &= C \quad \text{[Formula 7]}\\ &= \frac{\ln 2}{4\pi^2} \text{ esu/cm}\\ &= \frac{\varepsilon_0 \ln 2}{\pi} \ F/m\\ &= 0.00195354904 \text{ pF/mm}\end{aligned}$$

The dielectric constant in vacuum $\varepsilon_0$ becomes the relationship expressed by the following formula 8.

$$\begin{aligned}\varepsilon_0 &= \frac{1}{\mu_0 c^2}\\ &= 8.854187818 \times 10^{-12} (F/m)\end{aligned}$$

Here, $\mu_0$ means a permeability in vacuum and is $4\pi \times 10^{-7}$ (H/m), and c is the speed of light, which is 299792458 m/s in vacuum, these are basic constants of which the uncertainty is zero (0). From this, it can be understood that the electric capacity is determined only by the measurement of the lengths of the electrodes.

Figure 3:
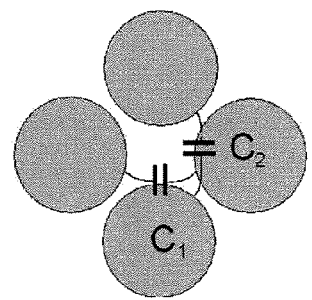
FIG. 3 is a conceptual view illustrating electrodes of a cross capacitor used as a sensor in the apparatus as shown in FIG. 2.

FIG. 3 is a conceptual view illustrating electrodes of a cross capacitor used as a sensor in the apparatus as shown in FIG. 2.

Thus, as shown in FIG. 3, when the cross-section of the cylinder is divided into four narrow insulator gaps, the capacitances $C_{ac}$ and $C_{bd}$ between electrodes facing each other have the relationship expressed by the following formulas 9 and 10.

$$\exp(-\pi C_{ac}/L\varepsilon_0) + \exp(-\pi C_{bd}/L\varepsilon_0) = 1 \quad \text{[Formula 9]}$$

$$C = \frac{\varepsilon_0 \cdot \ln 2}{\pi} \times L = 0.001953549 \text{ pF/mm} \quad \text{[Formula 10]}$$

Here, L becomes a length in the axial direction of the cylinder. Like the formula 10, the cross capacitance has no relation with the dimension of the electrodes and depends on only the axial length of the electrodes facing each other. These properties are applied to the sensor 10 for detecting whether the stator winding of the generator absorbs moisture.

In other words, when the principle of the cross capacitance is utilized, the effect due to a small quantity of dielectric substance existing between the surface of the stator winding of the generator and the sensor is weak and can be disregarded.

When the high electrode, the ground electrode, the low electrode, and the ground electrode are repeatedly arranged as the electrodes of the sensor employing the cross capacitance, the electrodes serve as electrodes of a quasi-cross capacitance.

When the electrodes are made in the planar type electrodes, the structure of the electrodes becomes simple, the close attachment to the surface of an object to be measured and the shielding are easily carried out.

Figure 5:
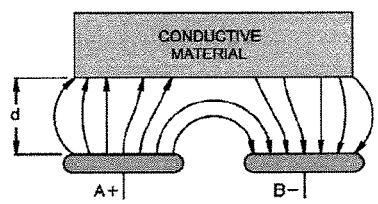
FIG. 5 is a conceptual view illustrating the structures of planar type electrodes.
Figure 5:
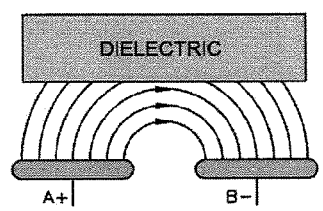

FIG. 5 is a conceptual view illustrating the structures of the planar type electrodes.

The planar electrodes, as shown in FIG. 5, are basically structured such that the high electrode and the low electrode are placed on the same plane. Thus, electric flux is formed as shown in FIG. 5 and upper and lower electrodes are arranged to face each other like in the conventional art so that the problem in the conventional art that the thickness of the object to be measured becomes the main cause of error can be solved.

Figure 6:
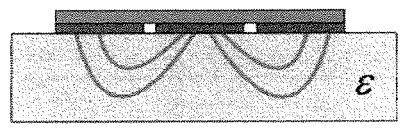
FIG. 6 is a conceptual view illustrating a flexible electrode.
Figure 6:
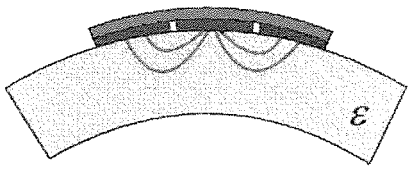

FIG. 6 is a conceptual view illustrating a flexible electrode.

Thus, when the planar type electrodes are formed on the surface of a flexible material, an object in FIG. 6 can be measured. In other words, in order to measure a dielectric property of a certain material, the material is made in the form of a planar plate and electrodes must be formed on the surfaces of the material. However, when this sensor 10 is used, the sensor 10 is closely contacted to the surface of an object so that the dielectric constant can be directly measured.

Moreover, for the repeatability and stability in the present invention, the measuring device employs a transformer ratio arm bridge, uses a measuring frequency of 1 kHz, and employs a two-terminal-pair type wiring of the measuring device.

Moreover, when applying the principle of the cross capacitor, there are features and advantages different from a case of employing a parallel-plate capacitor as follows. In other words, the measuring device has no relation with the manufacturing tolerance, sizes of respective electrodes, a degree of symmetry, and a degree of parallelism of the electrodes, is unaffected by uniformity, flatness, and rust of the surfaces of the electrodes, and depends on only the axial lengths L of the electrodes.

Figure 7:
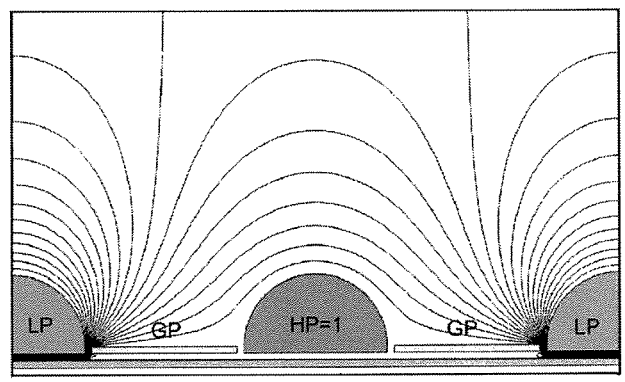
FIG. 7 is a conceptual view illustrating a simulation result carried out using a quasi-cross capacitor.

FIG. 7 is a conceptual view illustrating a simulation result carried out for the quasi-cross capacitor.

When the cross capacitance between electrodes that face each other is measured, another pair of electrodes must be grounded. In order to apply such a requirement to the sensor, when the electrodes are arranged in the order of the high voltage electrode, the ground electrode, the low voltage electrode, and the ground electrode, as shown in FIG. 7, an electrode shape of the quasi-cross capacitor is formed. However, the output of single cross capacitance is 0.001953 pF/mm as expressed by the formula 10, which is too small a value for processing a signal in the electronic circuit. Therefore, in order to increase output capacitance, as shown in FIG. 8, the electrodes that are repetitively arranged in the order of the high voltage electrode, the ground electrode, the low voltage electrode, and the ground electrode (H-G-L-G) are designed.

Figure 8:
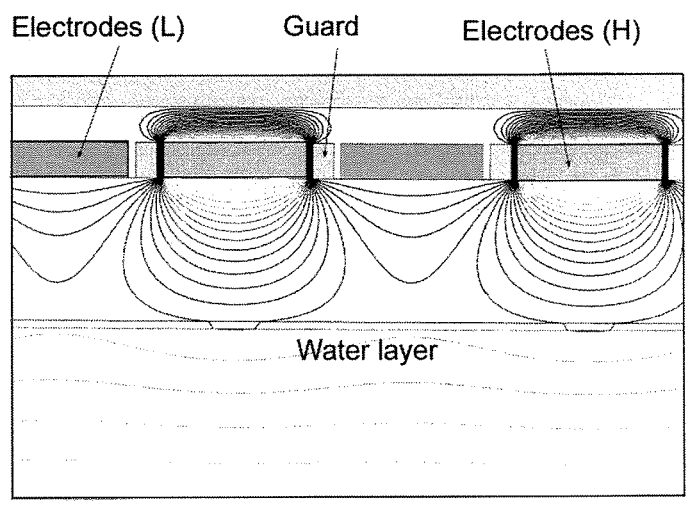
FIG. 8 is a conceptual view illustrating a simulation result carried out using electromagnetic field to design the sensor in FIG. 2.

FIG. 8 is a conceptual view illustrating a simulation result carried out using electromagnetic force to design the sensor in FIG. 2.

In FIG. 8, curved lines mean equipotential surfaces drawn using the values estimated by field simulations.

3. Design of Sensor

FIG. 9 is a sectional view illustrating configurations of various cross capacitors employed in the sensor in FIG. 2. In FIG. 9, FIG. 9a is a sectional view illustrating the overall sensor 10 employing the cross capacitor.

Figure 9A:
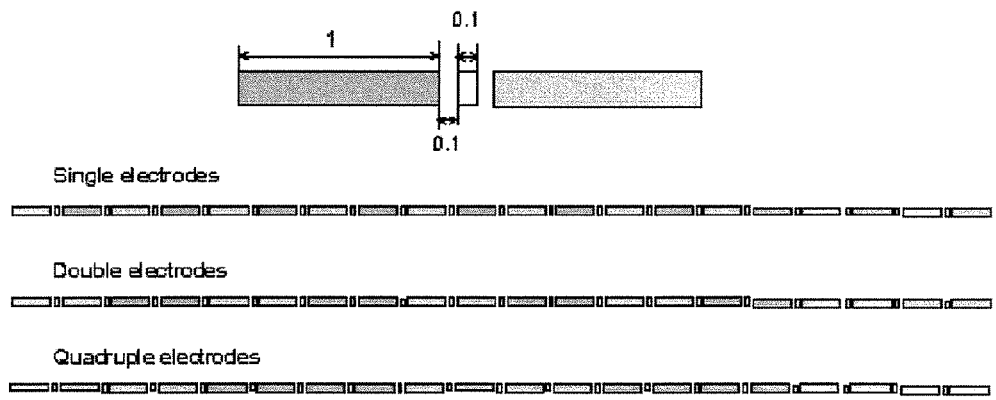
FIG. 9a-9e are the sectional view illustrating configurations of various cross capacitors employed in the sensor in FIG. 2.

Thus, as shown in FIG. 9a, when the electrode is used as H-L electrodes, the electrode is referred to as the "single" electrode. When the electrode is used as HH-LL electrodes, the electrode is referred to as the "double" electrode. When the electrode is used as HHHH-LLLL electrodes, the electrode is referred to as the "quadruple" electrode. This is for developing a sensor that is capable of estimating that the moisture in the inner copper conductor of the winding penetrates a Mica insulator with a thickness of 4.5 mm and exists in which position among an upper region, an intermediate region, and a lower region. In particular, a guard electrode having a width of 0.1 mm is inserted between electrode elements to form quasi-cross capacitance and, at the same time, the stray capacitance generated between adjacent electrodes is removed.

Figure 9B:
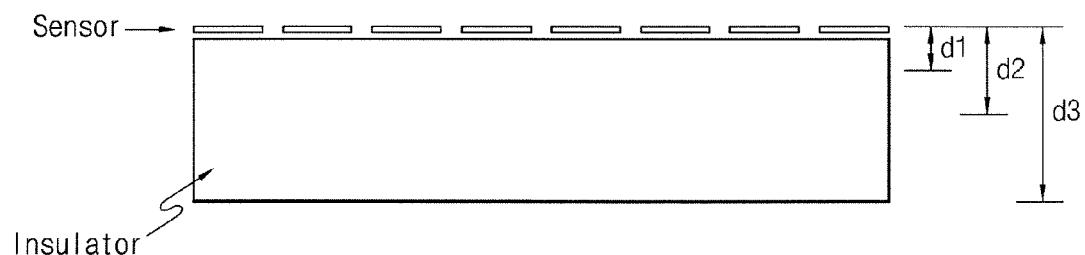
Figure 9C:
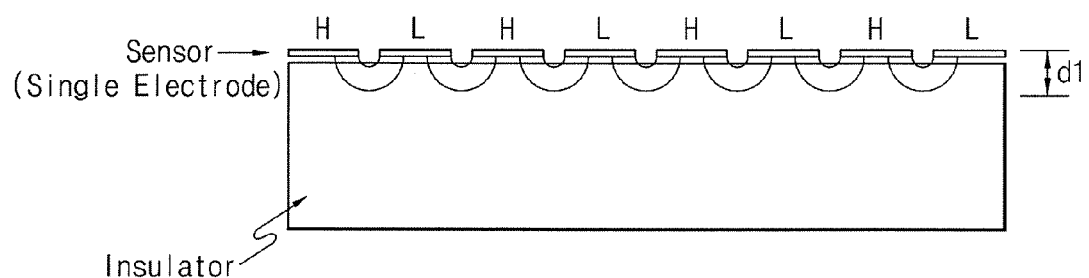
Figure 9D:
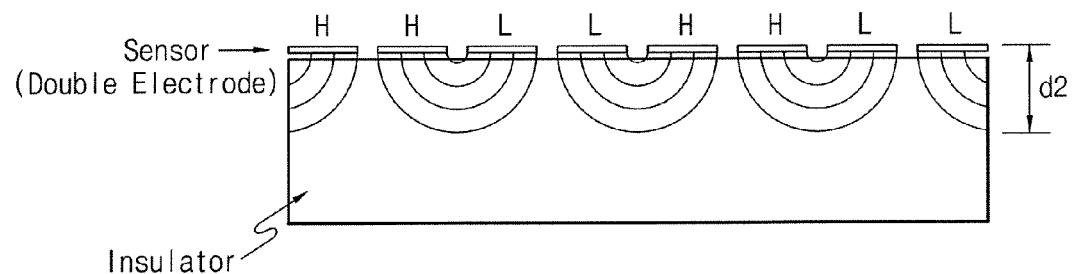
Figure 9E:
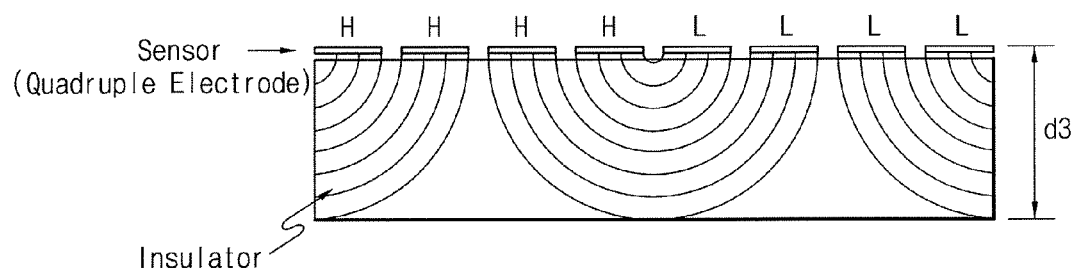

FIG. 9b illustrates the thicknesses d1, d2, and d3 of electrodes when the electrodes of the sensor measure the capacitance of an insulating material. FIG. 9c illustrates the thickness d1 of the single electrode. FIG. 9d illustrates the thickness d2 of the double electrode. FIG. 9e illustrates the thickness d3 of the quadruple electrode.

Therefore, when the insulator of the stator winding of a power generator is measured according to thickness, first, the sensor 10 becomes the single electrode to measure the capacitance corresponding to the thickness d1 of the single electrode as shown in FIG. 9c. Then, the sensor 10 becomes the double electrode to measure the capacitance corresponding to the thickness d2 of the double electrode as illustrated in FIG. 9d. Finally, the sensor 10 becomes the quadruple electrode to measure the capacitance corresponding to the thickness d3 of the quadruple electrode as illustrated in FIG. 9e.

Figure 10:
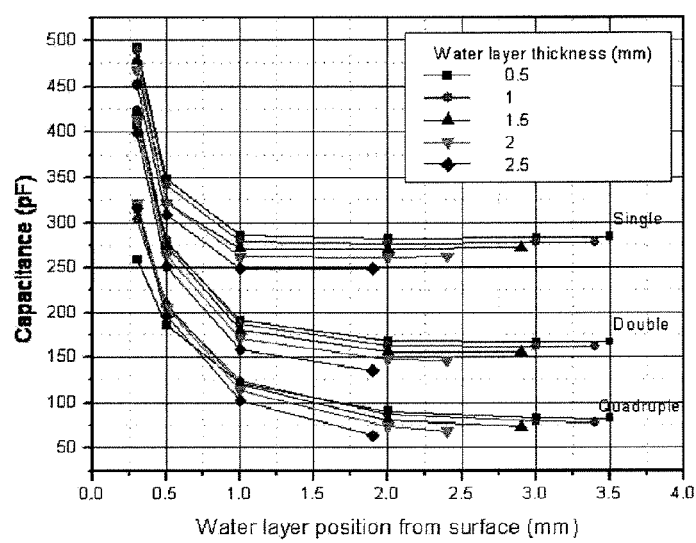
FIG. 10 is a graph illustrating a simulation result according to positional variation of a water layer in FIG. 9.

FIG. 10 is a graph illustrating a simulation result according to positional variation of a water layer in FIG. 9. FIG. 10 illustrates the field simulation results.

As shown in FIG. 10, the capacitance starts to increase when the water layer increases from the lower end to about 3.5 mm in the single electrode, when the water layer increases from the lower end to about 2.5 mm in the double electrode, and when the water layer increases from the lower end to about 1 mm to 1.5 mm in the quadruple electrode.

Figure 11:
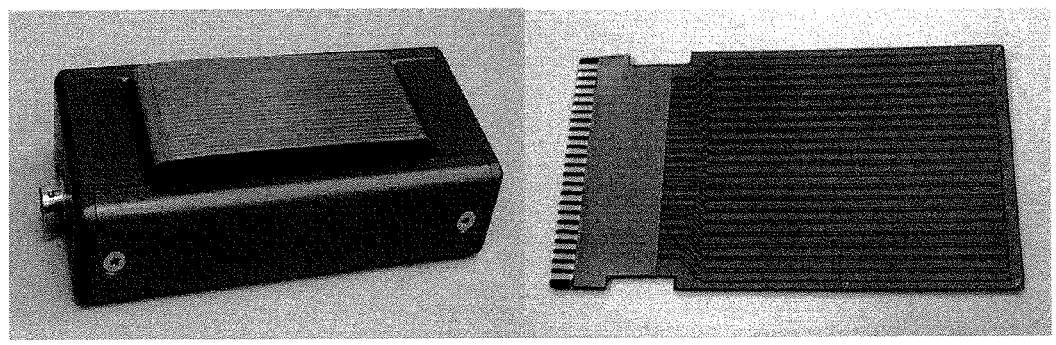
FIG. 11 is a view showing an example of the actual structure of the apparatus for testing water absorption in FIG. 2.

FIG. 11 illustrates an example of the actual structure of the apparatus for testing water absorption of FIG. 2, which illustrates two types of cross capacitors, that is, a cross capacitor in which a sensor driving circuit is designed together with a sensor and a cross capacitor in which a sensor driving circuit and a sensor are separated from each other.

In the designing of the sensor 10, as field simulation conditions, for convenience sake, the dielectric constant of the Mica is set to 4 and the dielectric constant of a water screen is set to 90. However, actually, when the water is absorbed into the Mica, the dielectric constant of the Mica increases from 4 to about 12.

After the optimal measurement conditions of the sensor 10 are confirmed through the field simulations, various sensors 10 are manufactured as illustrated in FIG. 11 using processes of manufacturing a flexible printed circuit board (FPCB).

When the surface of the sensor 10, is formed of a stiff material, since the surface of the winding of the power generator is significantly rough, when the sensor 10 is connected to the surface of the winding, an air gap inevitably exists so that a measurement error is generated. In order to minimize the measurement error, the sensor 10 is manufactured as a flexible sensor. A relay is used in the sensor including electrode devices so that the single, double, and quadruple electrodes are automatically selected.

In addition, a perfect shielded electrode is inserted into the rear surface of the sensor 10 to intercept the electric field generated on the rear surface so that it is possible to measure only the Mica characteristic on the front surface of the sensor.

4. Case of Designing a Circuit for Driving the Sensor Together with the Sensor 4-1. Designing and Manufacturing of Measuring Circuit FIG. 2 is a block diagram illustrating an apparatus for testing water absorption of an insulator of a stator winding of a power generator using cross capacitance according to a first embodiment of the present invention.

Therefore, the ratio transformer bridge, to be manufactured, is designed as illustrated in FIG. 2. In the manufactured measurement system, the circuit for driving the sensor is mounted in a single metal enclosure together with the sensor to minimize the stray capacitance and the influence of the electromagnetic noise and a display circuit capable of setting, modifying, and inputting the measured result in accordance with the menu is mounted in an additionally manufactured case.

Thus, when the sensor is attached to each surface of the stator windings of the power generator, the single electrode, the double electrode, and the quadruple electrode are automatically selected so that the measured result is displayed. When the button of the measuring device is pressed, the measured result is stored. At the same time, the sensor is connected to a personal computer as a main system 40 so that data is processed and analyzed by a computer.

Therefore, the sensor 10 measures the degree of water absorption of the insulator of the stator winding of the power generator according to the thickness.

The water absorption testing unit 20 processes the degree of water absorption of the insulator of the stator winding of the power generator that is measured by the sensor 10.

In the water absorption testing unit 20, the relay circuit 21 relays a signal between the sensor 10 and the central processing unit (CPU) 30 to receive a selection signal from the CPU 30 and to allow the sensor 10 automatically select the single, double, and quadruple electrodes.

The transformer bridge 22 receives the signal measured by the sensor 10 from the relay circuit 21 for relaying the signal of the sensor 10 to branch the received signal.

The oscillator (OSC) 23 is connected to the transformer bridge 22 to supply a local oscillation frequency.

A phase shifter 24 shifts the phase of the signal of the sensor 10 that is received from the transformer bridge 22 by 90 degrees based on the frequency received from the oscillator 23.

The first and second amplifiers (AMP) 25 and 26 receive the signal detected by the sensor 10 from the transformer bridge 22 to amplify the received signal.

The first detector (A/D) 27 converts the analog signal of the sensor 10 that is amplified by the first amplifier 25 into a digital signal to supply the digital signal to the CPU 30.

The second detector (A/D) 28 converts the analog signal of the sensor 10 that is amplified by the second amplifier 26 into a digital signal to be suitable for the phase shift by 90 degrees of the phase shifter 24 to supply the digital signal to the CPU 30.

Then, an A/D converter 29 converts the analog signal of the oscillator 23 into a digital signal to supply the digital reference signal to the CPU 30.

Then, the CPU 30 receives the signal of the sensor 10 that is converted into the digital signal from the first and second detectors 27 and 28, receives a reference signal from the A/D converter 29, and performs the water absorption test of the insulator of the stator winding of the power generator.

The interface unit 31 connects the main system 40 and the water absorption testing unit 20 to each other using the RS-232 method.

Then, the main system 40 can determine and manage the degree of water absorption of the insulator of the stator winding of the power generator that is detected by the sensor 10 through the water absorption testing unit 20.

4-2. Function of Display

Figure 12:
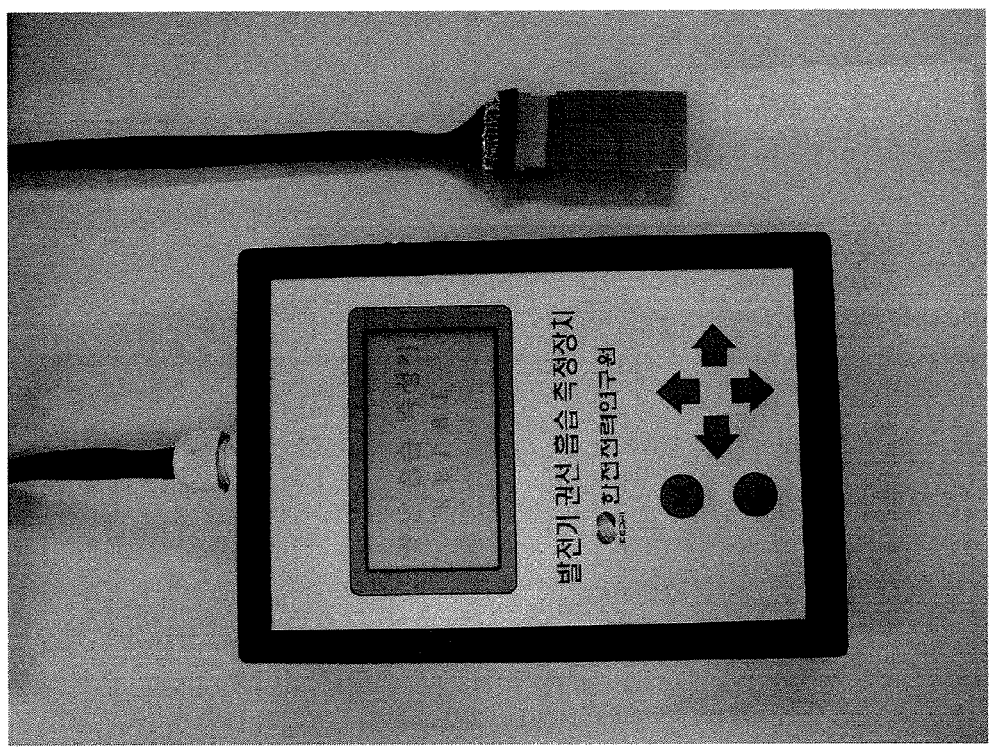
FIG. 12 is a view showing a real configuration of the apparatus in FIG. 2.

FIG. 12 is a view showing a real configuration of the apparatus in FIG. 2.

In FIG. 12, the main menus of Measurement, Data display, Data transmission, and Calibration are displayed on the display screen of the measurement system, which will be described in detail as follows.

(1) Measurement

This is a function of inputting information of a power station, a power generator, and measurement environments to be measured and of starting the measurement. That is, the list of the power stations of the whole country is input in the system so that it is possible to designate the power station to be measured, the unit number, the date of measurement, temperature of the winding, the number of windings, and the position of measurement can be designated. The position of measurement can be selected from CET-TOP, CET-OUT, CET-IN, CEB-OUT, CEB-IN, TET-TOP, TET-OUT, TET-IN, TEB-OUT, and TEB-IN.

(2) Data Display

This is a function of arranging and displaying the measured data as follows.

Measured Data Num=7

Gen_1 Measu: 72

CET-TOP Temp: 28° C.

Date: Dec. 12, 2004. 14:00

(3) Data Transmission

It is selected whether the measured and stored data are to be moved to the PC.

(4) Calibration

The manufactured measurement circuit determines capacitance and tan δ by comparing a capacitor device used as a reference capacitor and the capacitance measured by the sensor 10 as a capacitor to be measured with each other using the ratio transformer bridge circuit method to display the capacitance and the tan δ.

Therefore, the sensor system is calibrated with the lapse of a long time to obtain always the calibrated measurement result.

4-3. Designing and Manufacturing of Enclosure

Figure 13:
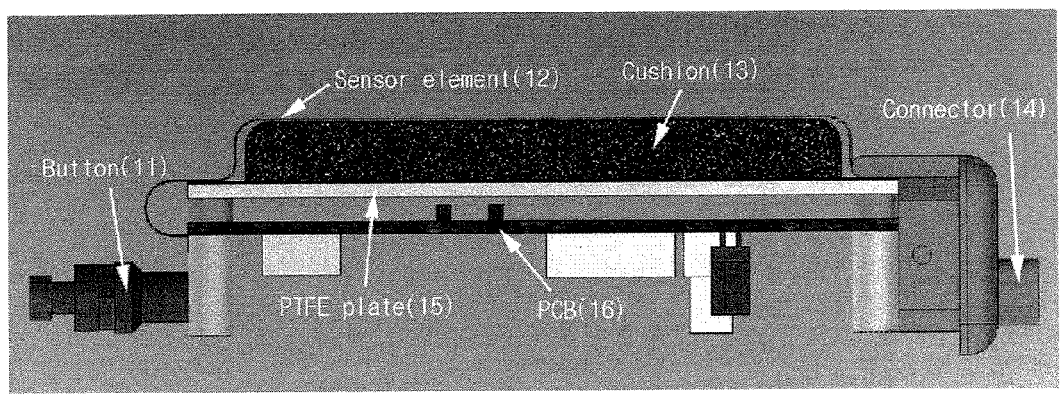
FIG. 13 is a side view of the sensor in FIG. 2.

FIG. 13 is a side view of the sensor in FIG. 2, which illustrates an example of the designing of an enclosure.

A sensor device mounted in a circuit board is provided in an enclosure so that the sensor device can be easily used. In order to closely attach a flexible sensor to the surface of the winding, a cushion is provided in the enclosure. The sensor is bent to be inserted into and fixed to a socket of a printed circuit board (PCB) 16. A shield plate on the rear surface of the sensor and all of the guard electrodes among the sensor elements are simultaneously connected to the ground of the circuit.

In FIG. 13, reference numerals 11, 12, 13, 14, 15, and 16 are assigned to a button, a sensor element, a cushion, a connector, a polytetrafluoroethylene (PTFE) plate, and a PCB, respectively.

5. Case of Designing the Circuit for Driving the Sensor to be Separated from the Sensor It is necessary to change the size and shape of the sensor in accordance with the position of measurement of the stator winding of the power generator. The sensor in which the sensor driving circuit is separated from the sensor is improved as shown in FIG. 11.

The following research on improvement was pursued in order to solve the problems found in the power station.

(1) The length of the flexible sensor is reduced from current 70 mm to 40 mm to design and manufacture the flexible sensor again and a silicon rubber plate having a thickness of 3 mm is attached to the flexible sensor so that the flexible sensor can be directly connected to the winding having the rough surface.

(2) When the length of the sensor is reduced, since the value of the internal standard capacitor of the bridge circuit changes, the sensor is manufactured and provided again.

(3) All of the circuits such as the bridge circuit and the pre-amplifier circuit that were provided on the rear surface of the previous sensor are moved to the previous enclosure.

(4) The electrical wiring lines between the sensor elements and the circuit are connected to each other by a coaxial cable to minimize external noise.

6. Inspection 6-1. On-The-Spot Inspection

Figure 14:
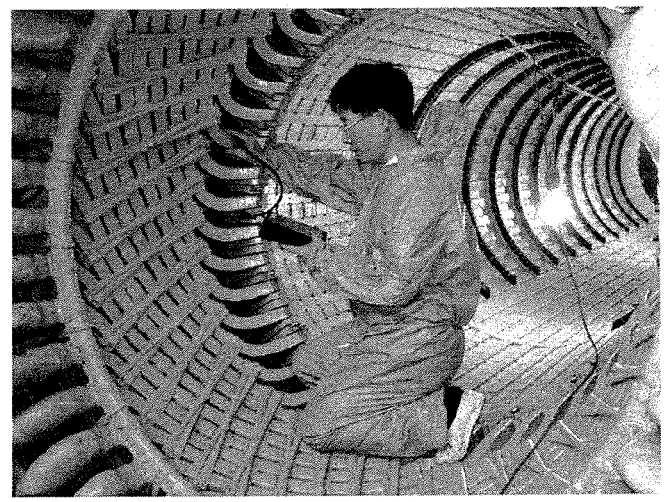
FIG. 14 is a view illustrating the water absorption test carried out on the insulator of a stator winding of a power generator using the apparatus in FIG. 2.

FIG. 14 is a view illustrating the water absorption test carried out on the insulator of a stator winding of a power generator using the apparatus in FIG. 2.

6-2. Measurement Result

Figures 15, 16:
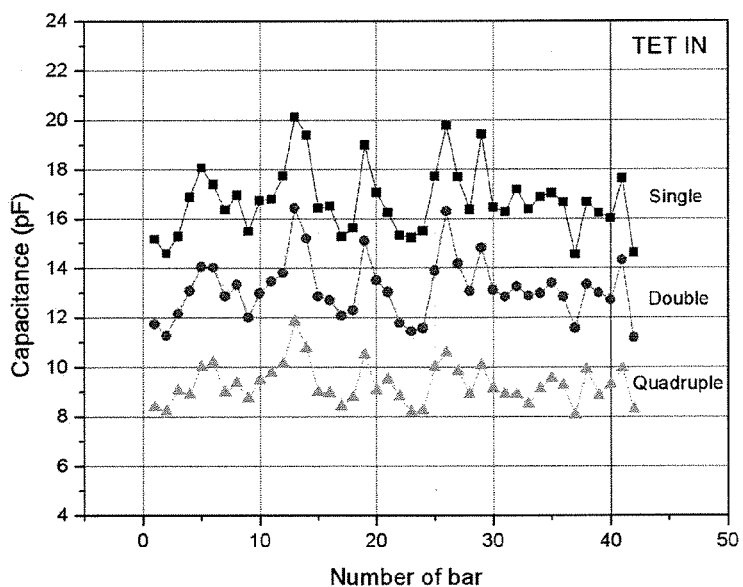
FIG. 15 is a graph illustrating distribution of capacitance measured by the apparatus in FIG. 2.
FIG. 16 is a table listing measured results in a case of designing a circuit for driving the sensor in FIG. 12 independently from the sensor.

The measurement result in the Samcheonpo power station, the Republic of Korea, is illustrated in FIG. 15 using the sensor manufactured.

FIG. 15 is a graph illustrating distribution of capacitance measured by the apparatus in FIG. 2.

It is possible to measure the inner side and the external side where the stator winding of the power generator is bent and to measure the capacitance of the insulator of the winding according to the thickness using the sensor as shown in FIG. 15.

6.3 Inspection by Standard Institution

In order to inspect the manufactured sensor and system, the national standard institution was requested to authenticate the testing apparatus. For authentication, a ceramic specimen unaffected by temperature and humidity was manufactured.

FIG. 16 is a table listing measured results in a case of designing a circuit for driving the sensor in FIG. 12 independently from the sensor, and FIG. 17 is a table listing measured results in a case of designing a circuit for driving the sensor in FIG. 12 by considering the sensor.

Therefore, in the experiment, the values measured by the system manufactured using the three kinds of ceramic specimens and a standard capacitance measuring device (AH2500) are determined as an offset value and a corrected value C1 as listed in FIGS. 16 and 17 and a difference between the corrected value C1 and a designation value C2 obtained when the circuit is connected to the apparatus for testing water absorption of the insulator of the stator winding of the power generator is obtained.

Because of authentication, as listed in FIGS. 16 and 17, it is possible to obtain excellent results.

As described above, according to the present invention, an inferior winding is detected, by determining whether or not the insulator of the stator winding of a power generator absorbs cooling water, according to thickness, using the cross capacitance, such that a power station is prevented from being suddenly stopped, costs for the maintenance are reduced, and the lifespan of the power generator is extended.

As described above, in the apparatus for testing water absorption of an insulator of a stator winding of a power generator using a cross capacitance according to the present invention and the method thereof, an inferior winding is detected, by determining whether or not the insulator of the stator winding of a power generator absorbs cooling water, according to thickness, using the cross capacitance, such that a power station is prevented from being suddenly stopped, costs for the maintenance are reduced, and the lifespan of the power generator is extended.

Moreover, since the apparatus for testing water absorption of an insulator of a stator winding of a power generator using a cross capacitance according to the present invention and the method thereof are applied to the test of the power station and it is determined whether the stator winding absorbs cooling water to prepare a countermeasure for the winding that absorbs water, it is possible to prevent the power generator from being damaged and to improve the reliability of the power station.

If the stator winding is damaged, it takes a long time to repair the winding. Therefore, it is possible to save expenses by determining whether the insulator of the winding absorbs water.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus of water absorption for generator stator winding insulator using a cross capacitance, comprising:
    a sensor by a cross capacitance; and
    a water absorption testing unit for carrying out the water absorption test of the insulator of the stator winding of the power generator using the sensor, wherein the water absorption testing unit comprises:
    a relay circuit for relaying a signal between the sensor and a CPU;
    a transformer bridge for receiving a signal from the sensor through the relay circuit and branching the same;
    an oscillator connected to the transformer bridge to supply a local oscillator frequency;
    a phase shifter for shifting a phase of the signal from the sensor received from the transformer bridge by 90 degrees with reference to the frequency received from the oscillator;
    first and second amplifiers for receiving a signal detected by the sensor from the transformer bridge and amplifying the same;
    a first detector for transforming an analog signal of the sensor amplified by the first amplifier into a digital signal;
    a second detector for transforming an analog signal of the sensor amplified by the second amplifier into a digital signal required for the 90 degree phase shift by the phase shifter;
    an A/D converter for converting the analog signals of the oscillator into digital signals;
    the CPU for receiving the signals of the sensor converted into the digital signals by the first and second detectors and a reference signal from the A/D converter and for carrying out the water absorption test of the insulator of the stator winding of the generator; and
    an interface for connecting a main system to the water absorption testing unit.

2. The apparatus of water absorption according to claim 1, wherein the CPU automatically switches and selects the single electrode, the double electrode, and the quadruple electrode of the sensor through the relay circuit.

3. The apparatus of water absorption according to claim 1, wherein the water absorption testing unit comprises a display connected to the CPU to display a result measured by the CPU.

4. The apparatus of water absorption according to claim 1, wherein the display selects and displays at least one of menus such as (1) Measurement, (2) Data display, (3) Data transmission, and (4) Calibration as a main menu.

* * * * *